United States Patent [19]

Godard et al.

[11] Patent Number: 5,556,965
[45] Date of Patent: Sep. 17, 1996

[54] INTERMEDIATES FOR THE PREPARATION OF 6α, 9α-DIFLUORO STEROIDS

[75] Inventors: Jean-Yves Godard, Le Raincy; Philippe Mackiewicz, Livry Gargan; Denis Prat, Pantin; Christian Richard, Rosny-Sous-Bois, all of France

[73] Assignee: Roussel Uclaf, France

[21] Appl. No.: 441,330

[22] Filed: May 15, 1995

Related U.S. Application Data

[62] Division of Ser. No. 186,965, Jan. 26, 1994, Pat. No. 5,478,957.

[30] Foreign Application Priority Data

Feb. 5, 1993 [FR] France ................... 93 01275

[51] Int. Cl.⁶ ................... C07J 71/00
[52] U.S. Cl. ................... 540/87; 540/88
[58] Field of Search ................... 540/87, 88

[56] References Cited

U.S. PATENT DOCUMENTS 3,546,215 12/1970 Fried .
3,636,010 1/1972 Anner et al. .
3,828,080 8/1974 Phillipps et al. .
4,198,404 4/1980 Edwards et al. .

OTHER PUBLICATIONS

CA103:105215, Schmidlin, Mar. 27, 1985, EP 135476.

Primary Examiner—Rebecca Cook
Attorney, Agent, or Firm—Bierman & Muserlian

[57] ABSTRACT

A compound of the formula

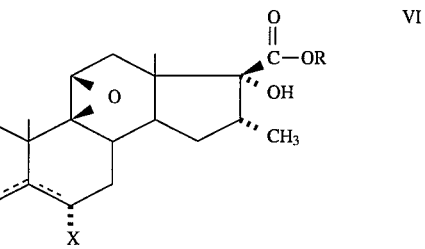

wherein R is hydrogen or an ester remainder, X is hydrogen or fluorine and Y combined with the doted lines represents

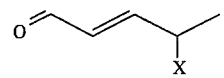

or X is hydrogen and and Y combined with the dotted lines is

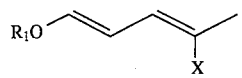

and $R_1$ is the remainder of an enol ether or ester.

1 Claim, No Drawings

INTERMEDIATES FOR THE PREPARATION OF 6α, 9α-DIFLUORO STEROIDS

PRIOR APPLICATION

This application is a division of U.S. patent application Ser. No. 186,965 filed Jan. 26, 1994, now U.S. Pat. No. 5,478,957.

OBJECTS OF THE INVENTION

It is an object of the invention to provide a novel process for the preparation of compounds of formula I and novel intermediates.

This and other objects and advantages of the invention will become obvious from the following detailed description.

THE INVENTION

The novel process of the invention a process for the preparation of a compound of the formula

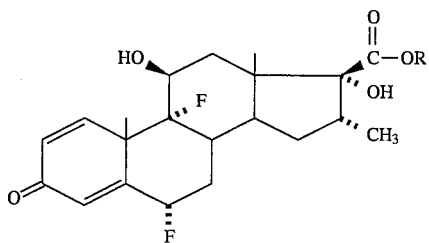

wherein R is hydrogen or an ester remainder comprises reacting a compound of the formula

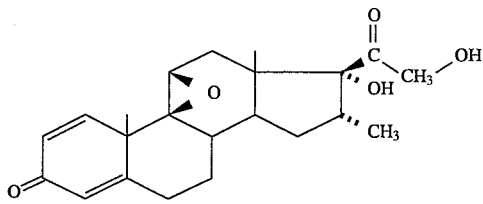

with an oxidizing degradation agent to obtain a compound of the formula

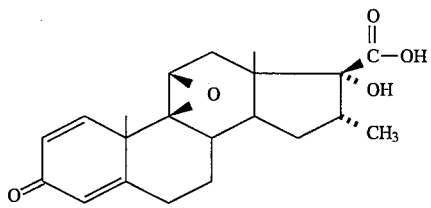

protecting the 3-ketone function in the form of the enol ether or ester and optionally the 17β-acid function in the form of an ester to obtain a compound of the formula

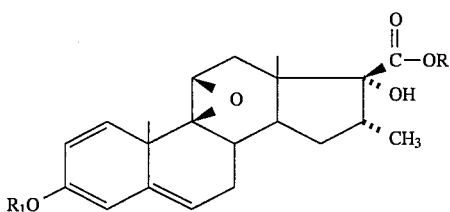

wherein R is defined as above and $R_1$ is a remainder of an enol ether or ester, reacting the latter with an electrophilic fluorination agent to obtain a compound of the formula

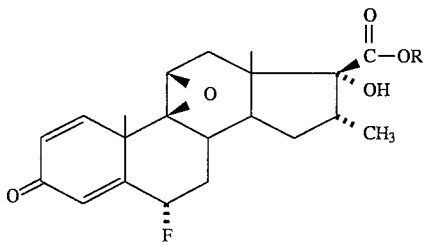

reacting the latter with a nucleophilic fluorination agent to obtain the compound of formula I and optionally when R is an ester remainder, saponifying the latter to obtain the corresponding acid.

By ester remainder is meant any remainder known to one skilled in the art and notably an alkyl of 1 to 6 carbon atoms, aryl of 6 to 10 carbon atoms or aralkyl of 7 to 12 carbon atoms.

When R is alkyl, it may be for example methyl, ethyl, propyl, isopropyl, n-butyl, sec-butyl, tert-butyl, pentyl or hexyl. When R is aryl, it may be for example phenyl or phenyl substituted by one or more alkyls. When R is aralkyl, it may be for example benzyl or phenethyl.

By ester remainder is also meant a silylated remainder, for example trialkylsilyl such as trimethyl-silyl, tert-butyl dimethyl-silyl or a triarylsilyl remainder such as triphenylsilyl or a diarylalkylsilyl such as diphenyl tert-butylsilyl.

By enol ether remainder in position 3 is meant any remainder known to one skilled in the art for blocking the 3-position in this form and particularly alkyl of 1 to 6 carbon atoms, for example methyl, ethyl or propyl, benzyl, tetrahydropyranyl or silylated group such as one of those mentioned above. By 3-enol ester remainder is meant a remainder of —COR, R being alkyl as defined above or aryl or aralkyl as defined above, and optionally substituted by at least one nitro, alkyl of 1 to 4 carbon atoms or halogen, especially chlorine.

In a preferred embodiment of the process of the invention, the 17β-acid function of the compound of formula III is protected to obtain a compound of the formula

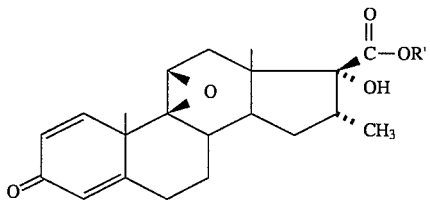

in which R' is an ester remainder, protecting the 3-ketone function of the latter compound in the form of an enol ether or ester to obtain a compound of formula IV as defined previously, in which R has the definition of R' indicated above and the synthesis is continued as indicated previously.

The protection of the 17β acid function can be carried out by either of the ester remainders mentioned above, preferably alkyl and methyl and ethyl being more preferred.

The protection of the 3-ketone function can be carried out by either an ether or ester remainder as mentioned above, an ester remainder being more preferred. Benzoyl optionally substituted by at least one nitro, chloro or methyl or acetyl, propionyl, butyryl or also valeryl can particularly be mentioned.

In a modification of the process of the invention in the same operation, the 3-ketone function and the 17β acid function are protected in the form of an enol ether and an enol ester respectively to obtain a compound of formula IV as defined previously, in which R and $R_1$ are the same protector group and the synthesis is continued as indicated previously. The protection in position 3 and 17 is then preferably carried out in the silylated ether and ester form respectively as defined above.

In a further modification of the process of the invention, only the 3-function is protected in an enol ether or ester form to obtain a compound of formula IV as defined previously in which R is hydrogen, then the synthesis is continued as indicated previously. The protection in position 3 is then preferably carried out in an enol ester form as mentioned above.

The oxidizing degradation agent used in the process can be for example periodic acid, lead tetracetate, potassium permanganate, hydrogen peroxide, catalytic periodic acid used in the presence of hydrogen peroxide, the alkali metal persulfates such as oxone$^R$ ($2KHSO_5$-$KHSO_4$-$K_2SO_4$ triple salt) or potassium monopersulfate. Periodic acid is particularly preferred.

For the various blockings in position 3 and 17 mentioned above, the corresponding reagents and their uses are known to one skilled in the art. The blocking in the ester form in position 17 could be carried out by the action of an alcohol in an acid medium or in the presence of dicyclohexylcarbodiimide and 4-dimethylaminopyridine, or in the case of a methyl ester, by the action of diazomethane, methyl sulfate or methyl carbonate.

It may be advantageous to operate in heterogeneous phases in the presence of a phase transfer catalyst, which can be particularly a quaternary ammonium salt such as tetrabutylammonium bromide, triethylbenzylammonium chloride or tricaprylmethylammonium chloride, or a phosphonium salt. The organic solvent used can be a chlorinated solvent like chloroform, methylene chloride or dichloromethane, an aromatic solvent like toluene, xylene or benzene, or an aliphatic or cycloaliphatic solvent like hexane or cyclohexane.

The blocking in the 3-enol ester form can be carried out by the action of an appropriate acid chloride operating in the presence of a nitrogenous base or by transesterification using an enol ester, for example an acetate of the following type

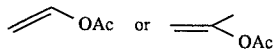

The blocking in the enol ether form could be carried out by the action of an alkyl halide in an alkaline medium, or by the action of dihydropyran, an alkyl orthoformate or an alcohol in an acid medium.

The 17β-blockings in the ester form and in position 3 in the enol ether form can also be carried out in the same operation, quite particularly in the case of a blocking in the form of a silylated ester and ether by the action of a suitable halide. It should be noted that in such a case, the particularly labile character of the silylated ester will involve the return to the acid from the hydrolysis which follows the 6-fluorination.

The fluorination agent used in the process must be an electrophilic agent. Examples are perchloryl fluoride, trifluoromethane sulfonyl fluoride and its derivatives, N-fluoropyridinium pyridine heptafluorodiborate, acetyl or trifluoroacetyl hypofluorite, N-fluoropyridinium, N-fluoro sulfonamides or N-fluoro sulfonimides, for example N-fluoro-benzene sulfonimide or, preferably, Selectfluor R or N-fluoro-N-chloromethyl triethylene diamine bis tetrafluoroborate. The operation is carried out in a solvent such as tetrahydrofuran, acetone, methylene chloride, toluene, and, especially in the case of fluorination by Selectfluor$^R$, in a protic or non-protic polar solvent such as dimethylformamide, methanol or, preferably, acetonitrile and, preferably also in the presence of water. The temperature of the reaction is either ambient temperature or a lower temperature and the reaction can be carried out in the presence of a phase transfer catalyst, notably one of those mentioned above, and optionally a cosolvent, especially a chlorinated solvent such as mentioned above.

The electrophilic fluorination in position 6 involves, after hydrolysis, the deblocking of the 3-ketone and the return to the system of $\Delta 1, 4$ double bonds.

The nucleophilic fluorination agent which is reacted on the compound of formula V is preferably hydrofluoric acid, especially aqueous hydrofluoric acid, or the complex of hydrofluoric acid with tetrahydrofuran, or, preferably, dimethylformamide. The operation is carried out at a temperature between $-10°$ and $+25°$ C. with or preferably without the presence of a cosolvent.

The optional final saponification is carried out according to techniques known to an average man skilled in the art. There can be mentioned hydrolysis or an alcoholysis in the presence of a base, for example an alkali metal or alkaline-earth metal hydroxide or a suitable nitrogen base.

Also an object of the invention are the new industrial compounds of the formula

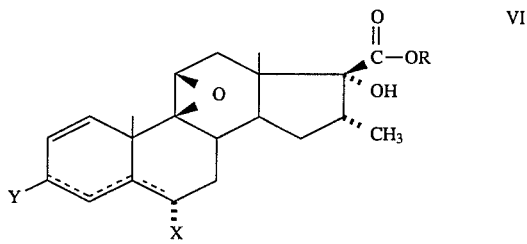

in which R is defined as previously, X is hydrogen or fluorine and Y combined with the dotted lines is a 3-keto-$\Delta 4$ system or X is hydrogen and Y combined with the dotted lines is a 3-$OR_1$-$\Delta 3,5$ system, $R_1$ being defined as previously.

The compound of formula II is described in U.S. Pat. No. 3,947,409 and the compounds of formula I are described for example, in French Patent No. 2,026,919. The esters possess particularly anti-inflammatory properties.

In the following examples, there are described several preferred embodiments to illustrate the invention. However, it should be understood that the invention is not intended to be limited to the specific embodiments.

EXAMPLE 1

6α,9α-difluoro-16α-methyl-17β-methoxycarbonyl-Δ1,4-androstadien-11 β, 17α-diol-3-one

STAGE A 9,11β-epoxy-16α-methyl-17β-carboxy-Δ1,4-androstadien-17α-ol-3-one 200 g of 9,11β-epoxy-16α-methyl-Δ1,4-pregnadien-17α, 21-diol-3,20-dione and 800 ml of methanol were mixed together and then, 128.5 g of orthoperiodic acid were added at 40° C. maximum with stirring over 20 minutes. The suspension was stirred under an inert gas atmosphere at 23/25° C. for one hour and then it was poured into a mixture of 1000 ml of water, 2000 g of ice and 200 g of sodium metabisulfite over 5 minutes. The mixture was stirred at 0,+10° C. for 30 minutes, filtered and rinsed with water. After drying, 192 g of the expected product were obtained which was used as is for the following stage.

IR Spectrum (CHCl$_3$), Absorptions at 3600 cm$^{-1}$: OH; 1706 cm$^{-1}$: acid C=O; 1662, 1623, 1607 cm$^{-1}$: keto-3 Δ1,4.

NMR Spectrum (CDCl$_3$, 300 MHz, ppm) 0.97 (d): 16-CH$_3$; 1.09 (s): 18-CH$_3$: 1.45 (s): 19-CH$_3$; 3.21 (s): H$_{11}$; 3.94: OH; 6.19 (s): H$_4$; 6.23 (dd): H$_2$: 6.64 (d): H$_1$.

STAGE B:

9,11β-epoxy-16α-methyl-17β-methoxycarbonyl-Δ1,4 -androstadien-17α- ol-3 -one 192 g of the product of Stage A, 800 ml of methylene chloride and 4 g of tetrabutylammonium bromide were mixed together and 400 ml of 2N sodium hydroxide, then 45.8 ml of dimethyl sulfate were introduced under an inert gas atmosphere over 5 minutes at about +18° to +22° C. The reaction medium was stirred for 90 minutes, then decanted and the aqueous phase was re-extracted with methylene chloride. The combined organic phases were washed with water, concentrated to approximately 400 ml, then distillation was continued by replacing the methylene chloride with isopropyl ether. The product was left to cool to ambient temperature over one hour while maintaining stirring, then maintained for another hour under these conditions, followed by separation. The crystals were rinsed with isopropyl ether and dried to obtain 185.4 g of the expected product.

IR Spectrum (CHCl$_3$), Absorptions at 3600 and 3540 cm$^{-1}$: OH; 1743, 1713 and 1438 cm$^{-1}$: CO$_2$Me; 1662, 1624 and 1608 cm$^{-1}$: keto-3 Δ1,4.

NMR Spectrum (CDCl$_3$, 300 MHz, ppm) 0.93 (d): 16-CH$_3$; 0.98 (s): 18-CH$_3$; 1.44 (s): 19-CH$_3$; 2.97 (s): OH; 3.21 (t): H$_{11}$; 3.77 (s): CO$_2$CH$_3$; 6.15 (s): H$_4$; 6.19 (dd): H$_2$; 6.61 (d): H$_1$.

| Analysis: C$_{22}$H$_{28}$O$_5$: Molecular Weight = 372.5 | | |
|---|---|---|
| | C % | H % |
| Calculated | 70.9 | 7.6 |
| Found | 71.0 | 7.8 |

STAGE C:

3-benzoyloxy-9,11β-epoxy-16α-methyl-17β-methoxycarbonyl -Δ1,3,5-androstatriene-17α-ol 30 g of the product of Stage B, 75 mg of hydroquinone and 42 ml of pyridine were mixed at +20° to +22° C. under an inert gas atmosphere and after the mixture was heated to 70° C., 13 ml of benzyl chloride were added. The reaction medium was maintained at 70° C. for 6 hours and then allowed to return to 40° C. 30 ml of methanol were added, followed by stirring at 40° C. for 30 minutes, then allowing the mixture to return to ambient temperature. The solution was poured into a mixture of 300 ml water and 44 ml of 22° Bé hydrochloric acid and 270 ml of methanol were added. The mixture was stirred for one hour and the crystals were separated out, washed with water and dried to obtain 36.95 g of the expected product which was purified by dissolving it in 2 volumes of methylene chloride, adding 5 volumes of methanol and distilling off the methylene chloride. After returning to ambient temperature with stirring, then after one hour at 0° C., 24.97 g of the dry expected product were isolated.

IR Spectrum (CHCl$_3$) Absorptions at 3600 and 3540 cm$^{-1}$: OH; 1730 cm$^{-1}$: C=O; 1438 cm$^{-1}$: OCH$_3$; 1657, 1670, 1603 and 1585 cm$^{-1}$: aromatic C=C's.

NMR Spectrum (CDCl$_3$, 300 MHz, ppm) 0.94 (d, J=7): 16-CH$_3$; 0.98 (s): 18-CH$_3$; 1.28 (s): 19-CH$_3$; 3.11 (s): H in position 11: 3.78 (s): CO$_2$CH$_3$; 5.49 (d, J=10): H in position 1; 5.80 (dd): H in position 2; 5.8: H in position 6; 5.93 (s): H in position 4; 7.48: H meta; 7.61 (tt): H para; 8.08: H ortho.

| Analysis (C$_{29}$H$_{32}$O$_6$: 476.6) | | |
|---|---|---|
| | C % | H % |
| Calculated | 73.1 | 6.8 |
| Found | 72.9 | 6.9 |

STAGE D

6α-fluoro-9,11α-epoxy-16α-methyl-17β-methoxycarbonyl-Δ1,4-androstadien-17α-ol-3-one 20 g of the product of Stage C and 100 ml of acetonitrile were mixed together under an inert gas atmosphere and then 2 ml of water were added. The suspension was cooled to −1° to +1° C., then 17.4 g of N-fluoro-N-chloromethyl-triethylenediamine bis tetrafluoroborate were slowly added. At the end of the introduction, the suspension was stirred at −1° to +1° C. for one hour and then it was poured into a solution of 400 ml of water and 10 ml of 20% ammonium hydroxide. 0.4 g of sodium metabisulfite were introduced and stirring was continued for 30 minutes at ambient temperature. A sufficient quantity of 20% ammonium hydroxide was added if necessary to adjust the pH to 8 and then the crystals were separated out, washed with water, then dried to obtain 16.34 g of the expected product.

NMR Spectrum (CDCl$_3$, 300 MHz, ppm) 0.93 (d): CH$_3$-CH; 0.99 (s): 18-CH$_3$; 1.41 (s): 19-CH$_3$; 3.33(d): H epoxide; 3.78 (s) : -CO$_2$CH$_3$; 5.43 (dddd, J HF=49): H in position 6beta; 6.25 (dd): H in position 2; 6.44 (t) : H in position 4; 6.52 (dd): H in position 1.

| Analysis (C$_{22}$H$_{27}$FO$_5$: 390.45) | | | |
|---|---|---|---|
| | C % | H % | F % |
| Calculated | 67.67 | 6.97 | 4.87 |
| Found | 67.9 | 6.9 | 4.7 |

STAGE E

6α, 9α-difluoro-16α-methyl-17β-methoxycarbonyl-Δ1,4-androstadien-11β, 17α-diol-3-one 180 ml of hydrofluoric acid—dimethylformamide complex and 18 g of the product of Stage D were mixed together under an inert gas atmosphere and the mixture was stirred at 22° C. ±3° C. for 3 hours. Then, the solution was poured into a mixture at 0° to +2° C. of 1.8 liters of water and 9 ml of 22° Bé ammonium hydroxide. While maintaining the temperature below 10° C., 290 ml of 22Bé ammonium hydroxide were added over 30 minutes, that being the quantity necessary to maintain the pH at 4.5±0.5. The mixture was stirred for one hour while allowing the temperature to rise and then the reaction medium was rested one hour. The crystals were separated out, washed with water at neutral pH and dried to obtain 18.86 g of the crude expected product which was taken up in about 7 volumes of chloroform. After heating to reflux, about ⅔ of the chloroform was distilled off and then the remaining product was cooled slowly to 0° to +5° C. and maintained for one hour at this temperature. The crystals were separated out and dried to obtain 18.3 g of the expected product which must be desolvated. To do this, the crystals were introduced into 10 volumes of water and stirred while heating to 90° to 95° C. for 30 minutes while distilling off the chloroform. After cooling, the crystals were separated out, washed with water and dried to obtain 15.8 g of the product melting at 227° C. and having a specific rotation of $[\alpha]^{20}_D = +60°+1°$ (c =1% in DMF). %F calculated: 9.25, found: 9 to 9.2.

The hydrofluoric acid—dimethylformamide complex used at the start was prepared as follows:

210 ml of dimethylformamide were stirred for 10 minutes under an inert gas atmosphere at +19° to +21° C. and condensed hydrofluoric acid cooled to −15 to −20° C. was introduced slowly, allowing the temperature to rise to about 45° C. Then, this rise in temperature was limited to +50° to +60° C. by an external bath at −15° to −20° C. and in this way, a total of 250 g of hydrofluoric acid were added over 75 minutes. The solution was then stirred for a few minutes under an inert gas atmosphere, before the introduction of the steroid under the conditions indicated above.

EXAMPLE 2

6α, 9α-difluoro-16α-methyl-17β-carboxy-Δ1,4-androstadien-11β,17α-diol-3-one 7.9 g of the product of Example 1, 75 ml of methanol and 4 ml of water were mixed together under an inert gas atmosphere and then was stirred at ambient temperature for 10 minutes. 2.5 g of potassium hydroxide in 20 ml of water were added over 5 minutes and then the mixture was taken slowly to reflux. After 3 hours 30 minutes at reflux, the mixture was cooled to +50° C. and acetic acid was added until a pH of about 6 was obtained, that was approximately 3 ml. The solution was concentrated to about 40 ml and cooled to 20° C. Then, water was added and the crystals were separated out and washed with a methanol—water mixture, then with water and dried to obtain 7.3 g of the expected product which was purified by impasting hot in methanol and crystallization from acetone with treatment on activated charcoal to obtain the product with a specific rotation of $[\alpha]^{20}_D = +65.5°$ C. (c=1% in DMF).

Analysis: $C_{21}H_{26}F_2O_5$

|  | C % | H % | F % |
|---|---|---|---|
| Calculated | 63.79 | 6.63 | 9.61 |
| Found | 63.7 | 6.6 | 9.3 |

NMR Spectrum (CDCl₃, 300 MHz, ppm) 1.02 (d): CH₃; 1.26 (s): 18-CH₃; 1.58 (s): 19-CH₃; 4.40 (d,m): H in position 11; 5.40 (d,m): H in position 6; 6.33 (d): H in position 2; 7.18 (d): H in position 1; 6.43 (s): H in position 4.

IR Spectrum (Nujol) Absorptions at 3559–3541 cm⁻¹: OH; 1698–1661 cm⁻¹: C═O and conjugated C═O; 1615–1603 cm⁻¹: C═C.

Various modifications of the process of the invention may be made without departing from the spirit or scope thereof and it is to be understood that the invention is intended to be limited only as defined in the appended claims.

What is claimed is:

1. A compound of the formula

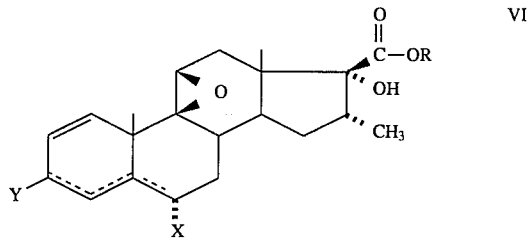

wherein R is hydrogen or an ester remainder, X is hydrogen or fluorine and Y combined with the dotted lines represents

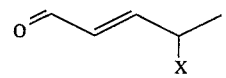

or X is hydrogen and Y combined with the dotted lines is

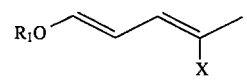

and $R_1$ is the remainder of an enol ether or ester.

* * * * *